United States Patent [19]

Kwak et al.

[11] Patent Number: 4,720,547

[45] Date of Patent: * Jan. 19, 1988

[54] PHOTOCHROMIC COMPOUND AND ARTICLES CONTAINING THE SAME

[75] Inventors: Won S. Kwak, Akron; Rodney J. Hurditch, Doylestown, both of Ohio

[73] Assignee: PPG Industries, Inc., Pittsburgh, Pa.

[*] Notice: The portion of the term of this patent subsequent to Jan. 20, 2001 has been disclaimed.

[21] Appl. No.: 826,428

[22] Filed: Feb. 5, 1986

Related U.S. Application Data

[63] Continuation-in-part of Ser. No. 635,696, Jul. 30, 1984, Pat. No. 4,637,698, which is a continuation-in-part of Ser. No. 548,600, Nov. 4, 1983, abandoned.

[51] Int. Cl.$^4$ ............................ G02B 5/23; G02F 1/01
[52] U.S. Cl. ........................................ 544/71; 252/586; 252/582; 350/354; 430/345; 351/163
[58] Field of Search .................. 252/586, 582, 600; 350/354; 351/163; 430/345; 544/71, 70

[56] References Cited

U.S. PATENT DOCUMENTS

| | | | |
|---|---|---|---|
| 3,407,145 | 10/1968 | Brule | 350/354 X |
| 3,562,172 | 2/1971 | Ono et al. | 252/600 |
| 3,578,602 | 5/1971 | Ono et al. | 252/600 |
| 3,843,550 | 10/1974 | Hinnen | 252/586 |
| 3,980,480 | 9/1976 | Laridon | 430/345 X |
| 4,215,010 | 7/1980 | Hovey et al. | 252/586 |
| 4,289,497 | 9/1981 | Hovey | 350/354 X |
| 4,342,668 | 8/1982 | Hovey et al. | 252/586 |
| 4,440,672 | 4/1984 | Chu | 252/586 |

FOREIGN PATENT DOCUMENTS 134633  3/1985  European Pat. Off. .

*Primary Examiner*—John F. Terapane
*Assistant Examiner*—Catherine Kilby
*Attorney, Agent, or Firm*—Irwin M. Stein

[57] ABSTRACT

Described are photochromic spiro[indoline-2,3'[3H]pyrido [3,2-f][1,4]-benzoxazine compounds having a $C_1$-$C_4$ monohaloalkyl or $C_1$-$C_4$ polyhaloalkyl substituent on the indoline ring, and their use in plastic hosts to impart a photochromic response thereto.

12 Claims, No Drawings

PHOTOCHROMIC COMPOUND AND ARTICLES CONTAINING THE SAME

CROSS REFERENCE TO RELATED APPLICATIONS

This application is a continuation-in-part application of our copending application, Ser. No. 635,696, filed July 30, 1984, now Pat. No. 4,637,698 which application is a continuation-in-part application of our application Ser. No. 548,600 filed Nov. 4, 1983, now abandoned.

DESCRIPTION OF THE INVENTION

The present invention relates to novel photochromic compounds, and to compositions and articles containing such photochromic compounds. Photochromism is a reversible phenomenon illustrated by a compound which, when exposed to the radiation of light involving ultraviolet rays such as sunlight or the light of a mercury lamp, changes color and then returns to its original color if the radiation is discontinued or the compound is stored in the dark. A compound illustrating this property is called a "photochromic compound".

Various types of photochromic compounds have been synthesized and suggested for use in applications in which a color change or darkening is induced by sunlight. In particular, spiro(indoline) naphthoxazine compounds, as described in U.S. Pat. Nos. 3,562,172, 3,578,602, 4,215,010, and 4,342,668, show particular advantages for sunglasses and ophthalmic lenses. Such photochromic compounds either in crystalline form or in a solution or dispersion in a transparent medium change rapidly from a colorless state to blue when exposed to sunlight or ultraviolet radiation and return to the original colorless state by being allowed to stand in the dark or in the absence of strong ultraviolet radiation.

DETAILED DESCRIPTION OF THE INVENTION

In accordance with the present invention, there are provided novel photochromic compounds represented by the following graphic formula,

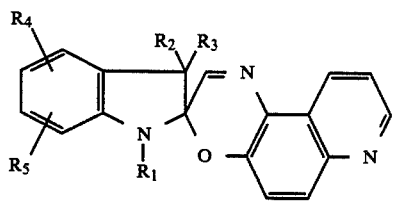

I

In the above graphic formula I, $R_1$ is selected from the group consisting of $C_1$–$C_8$ alkyl, phenyl, phen($C_1$–$C_4$)alkyl, allyl and mono- and disubstituted phenyl, said phenyl substituents being selected from $C_1$–$C_4$ alkyl and $C_1$–$C_5$ alkoxy. Preferably, $R_1$ is a $C_1$–$C_4$ alkyl, phenyl or benzyl radical.

$R_2$ and $R_3$ of formula I are each selected from the group consisting of $C_1$–$C_5$ alkyl, phenyl, mono- and disubstituted phenyl, benzyl, or $R_2$ and $R_3$ combine to form a cyclic ring selected from the group consisting of an alicyclic ring containing from 6 to 8 carbon atoms (including the spiro carbon atom), norbornyl and adamantyl. The phenyl substituents may be selected from $C_1$–$C_4$ alkyl and $C_1$–$C_5$ alkoxy radicals. Preferably, $R_2$ and $R_3$ are each selected from $C_1$–$C_5$ alkyl. When one of $R_2$ or $R_3$ is a tertiary alkyl radical, such as tertiary butyl or tertiary amyl, the other is preferably an alkyl radical other than a tertiary alkyl radical.

$R_4$ in graphic formula I is selected from the group consisting of hydrogen, $C_1$–$C_5$ alkyl, halogen, $C_1$–$C_5$ alkoxy, nitro, cyano $C_1$–$C_4$ monohaloalkyl, $C_1$–$C_4$ polyhaloalkyl, e.g., trihaloalkyl, and $C_1$–$C_8$ alkoxycarbonyl. $R_5$ in formula I is selected from the group consisting of $C_1$–$C_4$ monohaloalkyl and $C_1$–$C_4$ polyhaloalkyl, e.g., trihaloalkyl. $R_4$ and $R_5$ are independently located on any two of the available carbon atoms of the indolino portion of the compound, i.e., on the 4, 5, 6, or 7 positions. Preferably, when $R_4$ is other than hydrogen, the substituents $R_4$ and $R_5$ are present at the 4 and 5, 5 and 6, 4 and 7 or 6 and 7 carbon atoms of the indolino moiety. While any halogen, i.e., chlorine, bromine, iodine and fluorine may be used in respect to the halogen or haloalkyl substituents, chlorine and bromine, especially chlorine is preferred for the halogen and fluorine is preferred for the polyhaloalkyl, e.g., trifluoromethyl ($CF_3$). Preferably, $R_4$ is selected from the group consisting of hydrogen, $C_1$–$C_2$ alkyl, chlorine, fluorine, $C_1$–$C_2$ trihaloalkyl, e.g., trihalomethyl, and $C_1$–$C_5$ alkoxy; and $R_5$ is a $C_1$–$C_2$ trihaloalkyl, e.g., trifluoromethyl.

It is possible that the photochromic compound can be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole or mixtures thereof. Thus, when $R_4$ is hydrogen, the photochromic compound may be substituted at the 4 position on the indoline ring, at the 6 position of that ring or comprise a mixture of such isomers. When $R_4$ is other than hydrogen, the photochromic compound may be substituted at any combination of the 4, 5, 6, or 7 carbon atoms of the indoline ring (as heretofore indicated) and may comprise an isomeric mixture of such compounds, e.g., a mixture of compounds having substituents at the 4 and 5, and 6 and 5 positions of the indoline ring, or 4 (or 6) and any other available position of the indoline ring. Preferably, $R_5$ is located at the 4 (or 6) position and $R_4$ is at any of the other unsubstituted positions on the indoline ring, usually the 5 position or the 4 (or 6) position when such locations are unoccupied by the $R_5$ substituent.

Of particular interest, are photochromic compounds represented by graphic formula I wherein $R_1$ is a $C_1$–$C_4$ alkyl, such as methyl, ethyl, n-propyl, isopropyl, n-butyl, secondary butyl, isobutyl and tertiary butyl; $R_2$ and $R_3$ are each methyl, ethyl or phenyl; $R_4$ is trifluoromethyl, fluorine, chlorine, hydrogen, methyl or methoxy; and $R_5$ is trifluoromethyl.

Examples of compounds within the scope of graphic formula I are listed in Table I. Compound 1 may be named: 1,3,3-trimethyl-4 (or 6) trifluoromethylspiro[indoline-2,3'[3H]pyrido [3,2-f][1,4]-benzoxazine]. Compounds 2–12 may be similarly named as substituted spiro[indoline-2,3'-[3H]pyrido [3,2-f][1,4]-benzoxazines using the substituents described in Table I for such compounds.

TABLE I

| Compound No. | SUBSTITUENT | | | | |
|---|---|---|---|---|---|
| | $R_1$ | $R_2$ | $R_3$ | $R_4$ | $R_5$ |
| 1 | methyl | methyl | methyl | hydrogen | 4(6)-$CF_3$ |
| 2 | methyl | methyl | methyl | 4-$CF_3$ | 6-$CF_3$ |

TABLE I-continued

| Compound No. | SUBSTITUENT | | | | |
|---|---|---|---|---|---|
| | $R_1$ | $R_2$ | $R_3$ | $R_4$ | $R_5$ |
| 3 | methyl | methyl | methyl | 5-fluoro | 4(6)-$CF_3$ |
| 4 | methyl | methyl | methyl | 5-chloro | 4(6)-$CF_3$ |
| 5 | methyl | methyl | methyl | hydrogen | 5-$CF_3$ |
| 6 | methyl | methyl | methyl | 4(6)-methoxy | 6(4)-$CF_3$ |
| 7 | methyl | methyl | methyl | 5-methyl | 6-$CF_3$ |
| 8 | methyl | methyl | methyl | 4-$CF_3$ | 5-methyl |
| 9 | methyl | methyl | methyl | 7-methyl | 6-$CF_3$ |
| 10 | ethyl | methyl | methyl | hydrogen | 4(6)-$CF_3$ |
| 11 | ethyl | methyl | methyl | 4-$CF_3$ | 6-$CF_3$ |
| 12 | methyl | ethyl | methyl | 4-$CF_3$ | 6-$CF_3$ |
| 13 | methyl | ethyl | methyl | 5-fluoro | 4(6)-$CF_3$ |
| 14 | methyl | phenyl | methyl | 4-$CF_3$ | 6-$CF_3$ |
| 15 | methyl | phenyl | methyl | 5-fluoro | 4(6)-$CF_3$ |

The photochromic compounds of the present invention can be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine, and ethylene glycol. The compounds can also be dispersed in liquids containing water, alcohols and other solvents.

The photochromic compounds of the present invention can also be dissolved in colorless or transparent solutions prepared from transparent polymers, copolymers or blends of such transparent polymers and a suitable organic solvent, e.g., polymers of transparent host materials described hereinafter dissolved in one or more of the aforesaid described organic solvents. Examples of such solutions include a polyvinylacetate-acetone solution, a nitrocellulose-acetonitrile solution, a polyvinylchloride-methylethylketone solution, a polymethylmethacrylate-acetone solution, a cellulose acetate-dimethylformamide solution, a polyvinylpyrrolidone-acetonitrile solution, a polystyrene-benzene solution, and an ethyl cellulose-methylene chloride solution.

The aforesaid photochromic solutions or compositions can be applied to a transparent support, such as cellulose triacetate, polyethylene terephthalate or baryta paper and dried to obtain a photochromic material, which may be color formed by ultraviolet radiation and returned to colorless by removing the source of ultraviolet radiation.

The photochromic compounds of the present invention or compositions containing same can be applied to or incorporated within a solid transparent polymerized organic material, i.e., a synthetic plastic host material. Preferably, the host material is an optically clear material, e.g., materials suitable for ophthalmic elements, such as ophthalmic lenses, or materials useful for applications such as windows, windshields, etc. A host material containing the photochromic compounds of the present invention can be used in the preparation of photochromic plastic films, sheets and lenses, such as lenses for sunglasses, ski goggles, visors, camera lenses and filters. As used herein, the term "optical element" is meant to include lenses and transparencies.

Examples of transparent host materials which can be used with the photochromic compounds of the present invention include: polymers of polyol(allyl carbonate) monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethyleneterephthalate, polystyrene, poly(styrene-methylmethacrylate) copolymers, poly(styrene-acrylonitrile) copolymer, and polyvinylbutyral. Transparent copolymers and blends of the transparent polymers are also suitable as host materials. Preferably, the host material is an optically clear polymerized organic material prepared from a polycarbonate, such as poly(4,4'-dioxydiphenol-2,2-propane), which is sold under the trademark, LEXAN; a polymethylmethacrylate, such as the material sold under the trademark, PLEXIGLAS; polymerizates of a polyol(allyl carbonate), especially diethylene glycol bis(allyl carbonate), which is sold under the trademark, CR-39, and its copolymers with for example vinyl acetate, e.g., copolymers of from 80-90 percent diethylene glycol bis(allyl carbonate) and 10-20 percent vinyl acetate; particularly 80-85 percent of the bis(allyl carbonate) and 15-20 percent vinyl acetate, cellulose acetate, cellulose propionate, cellulose butyrate, polystyrene and its copolymers with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The polyol (allyl carbonate) monomers can be represented by the graphic formula:

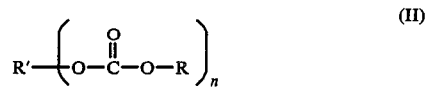

(II)

wherein R is the radical from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

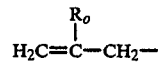

wherein $R_o$ is hydrogen, halogen, or a $C_1$–$C_4$ alkyl group. Specific examples of R include the groups: alkyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly, R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

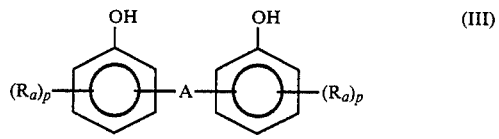

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), Ra represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, (—CH₂—CH₂—), trimethylene, methylethylene, tetramethylene, ethylethylene, pentamethylene, hexamethylene, 2-methylhexamethylene, octamethylene, and decamethylene; alkylene ether groups such as —CH₂—O—CH₂—, —CH₂CH₂—O—CH₂CH₂—, —CH₂—O—CH₂CH₂—, and —CH₂CH₂CH₂—O—CH₂CH₂CH₂—; alkylene polyether groups. such as —CH₂CH₂—O—CH₂CH₂—O—CH₂CH₂— and —CH₂CH₂CH₂—O—CH₂CH₂CH₂—O—CH₂CH₂CH₂—; alkylene carbonate and alkylene ether carbonate groups such as —CH₂CH₂—O—CO—O—CH₂CH₂— and —CH₂CH₂—O—CH₂CH₂—O—CO—O—CH₂CH₂—O—CH₂CH₂—; and isopropylidene bis(paraphenyl), i.e.,

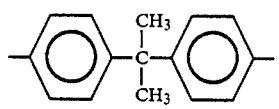

Most commonly, R' is —CH₂CH₂—, —CH₂CH₂—O—CH₂CH₂—, or —CH₂CH₂—O—CH₂CH₂—O—CH₂CH₂—.

Specific examples of polyol(allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

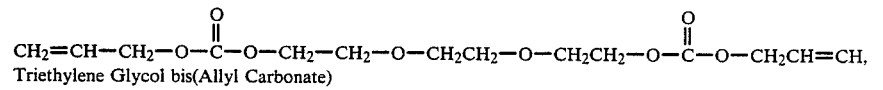

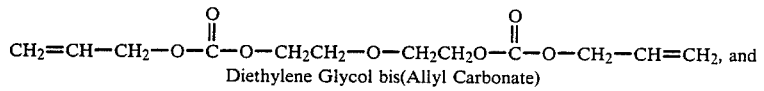

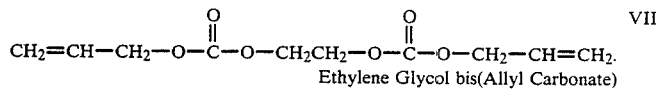

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

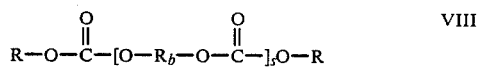

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

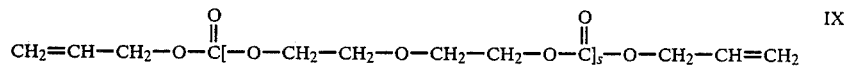

wherein s is a whole number from 2 to 5. The polyol(allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol(allyl carbonate) monomer can be used. In that embodiment, the monomer is thickened by heating or partially polymerized by using small, e.g., 0.5-1.5 parts of initiator per hundred parts of monomer (phm) to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

The amount of the photochromic compound or composition-containing same applied to or incorporated into a host material is not critical and depends generally upon the intensity of the color of the composition desired upon irradiation thereof and upon the method used to incorporate or apply the photochromic compound. Typically, the more compound added, the greater the color intensity. Generally such amount can be described as a photochromic amount. Usually, the amount of photochromic compound incorporated into the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 10.

Solutions of the photochromic compounds of the present invention undergo a change in color upon exposure to ultraviolet radiation and return to their original color or colorless state upon removal of the source of ultraviolet radiation. Such color change may be repeated numerous times.

The photochromic compounds or compositions of the present invention can be applied to or incorporated into a host material by methods known in the art. Such methods include dissolving or dispersing the compound in the host material, i.e., imbibition of the photochromic compound in the host material, by immersion, thermal transfer, or coating, and incorporation of the photochromic compound as a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds or compositions of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in water, alcohol or other solvents or solvent mixtures and then imbibed into the solid host material by immersion for from several minutes to several hours, e.g., 2-3 minutes to 2-3 hours of the host material in a bath of such solution or dispersion. The bath is conventionally at an elevated temperature, usually in the range of 50°–120° C. Thereafter, the host material is removed from the bath and dried;

(c) The photochromic compounds and compositions may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g, in an oven, for from a minute to several hours at temperatures in the range of from 80°–180° C.;

(d) In a variation of the above imbibition procedure, the photochromic compound or composition can be deposited onto a temporary support, e.g., a sheet of craft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of an adherent film by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of the host material.

The photochromic compounds of the present invention can be synthesized by reaction of the corresponding nitroso-hydroxy quinoline compound with the corresponding indoline (Fischer's base) or indolium salt, e.g., the iodide salt, compound. The two precursor materials are refluxed in a suitable solvent, such as toluene or isopropanol, containing a base, such as triethylamine, until the reaction is completed. The photochromic compound is recovered from the reaction mixture, e.g., by filtration, and recrystallized, if necessary, to obtain a more purified product.

For example, 3-trifluoromethylhydrazine may be condensed with 3-methyl-2-butanone in the presence of dilute sulfuric acid or powdered zinc chloride to produce 2,3,3-trimethyl-4 (and/or 6)-trifluoromethyl indole. The substituted indole may then be further reacted with methyl iodide to produce 1,2,3,3-tetramethyl-4 (and/or 6)-trifluoromethyl indolium iodide. A suspension of the iodide salt in toluene containing triethylamine and ethanol may then be added slowly to a heated suspension of 5-nitroso-6-quinolinol in toluene. The reaction mixture should be refluxed until the condensation reaction has been completed. Isopropanol may be substituted for the toluene in the above synthesis. The product may be named: 1,3,3-trimethyl-4 (and/or 6) trifluoromethylspiro[indoline-2,3'[3H]pyrido [3,2-f][1,4-benzoxazine].

Although the present invention has been described with reference to specific details of certain embodiments thereof, it is not intended that such detail should be regarded as limitations upon the scope of the invention except as and to the extent that they are included in the accompanying claims.

We claim:

1. A photochromic compound represented by the following graphic formula:

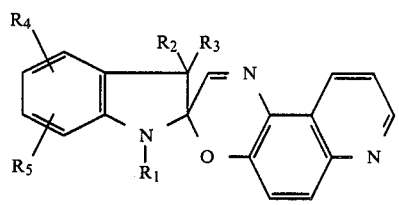

wherein:

(a) $R_1$ is selected from the group consisting of $C_1$–$C_8$ alkyl, phenyl, phen($C_1$–$C_4$)alkyl, allyl and mono- and di-substituted phenyl, said phenyl substituents being selected from $C_1$–$C_4$ alkyl and $C_1$–$C_5$ alkoxy;

(b) $R_2$ and $R_3$ are each selected from the group consisting of $C_1-C_5$ alkyl, phenyl, and mono- and di-substituted phenyl, benzyl or combine to form a cyclic ring selected from the group consisting of an alicyclic ring containing from 6 to 8 carbon atoms (including the spiro carbon atoms), norbornyl and adamantyl, said phenyl substituents being selected from $C_1-C_4$ alkyl and $C_1-C_5$ alkoxy;

(c) $R_4$ is selected from the group consisting of hydrogen, $C_1-C_5$ alkyl, halogen, $C_1-C_5$ alkoxy, nitro, cyano, $C_1-C_4$ monohaloalkyl, $C_1-C_4$ polyhaloalkyl and $C_1-C_8$ alkoxycarbonyl, and (d) $R_5$ is selected from the group consisting of $C_1-C_4$ monohaloalkyl and $C_1-C_4$ polyhaloalkyl.

2. A photochromic compound of claim 1 wherein:
(a) $R_1$ is selected from the group consisting of $C_1-C_4$ alkyl, phenyl and benzyl,
(b) $R_2$ and $R_3$ are each selected from $C_1-C_5$ alkyl,
(c) $R_4$ is selected from the group consisting of hydrogen, $C_1-C_2$ alkyl, chlorine, fluorine, $C_1-C_5$ alkoxy and $C_1-C_4$ trihaloalkyl, and
(d) $R_5$ is trihaloalkyl.

3. A photochromic compound of claim 1 wherein $R_1$ is $C_1-C_4$ alkyl, $R_2$ and $R_3$ are each methyl or ethyl, $R_4$ is chlorine, fluorine, trifluoromethyl, hydrogen, methyl, ethyl or methoxy, and $R_5$ is trifluoromethyl.

4. A photochromic article comprising a solid transparent polymerized organic host material containing a photochromic amount of a photochromic compound represented by the graphic formula:

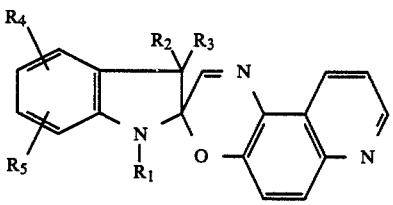

wherein:
(a) $R_1$ is selected from the group consisting of $C_1-C_8$ alkyl, phenyl, phen($C_1-C_4$)alkyl, allyl and mono- and di-substituted phenyl, said phenyl substituents being selected from $C_1-C_4$ alkyl and $C_1-C_5$ alkoxy;
(b) $R_2$ and $R_3$ are each selected from the group consisting of $C_1-C_5$ alkyl, phenyl, and mono- and di-substituted phenyl, benzyl or combine to form a cyclic ring selected from the group consisting of an alicyclic ring containing from 6 to 8 carbon atoms (including the spiro carbon atom), norbornyl and adamantyl, said phenyl substituents being selected from $C_1-C_4$ alkyl and $C_1-C_5$ alkoxy;
(c) $R_4$ is selected from the group consisting of hydrogen, $C_1-C_5$ alkyl, halogen, $C_1-C_5$ alkoxy, nitro, cyano, $C_1-C_4$ monohaloalkyl, $C_1-C_4$ polyhaloalkyl and $C_1-C_8$ alkoxycarbonyl; and
(d) $R_5$ is selected from the group consisting of $C_1-C_4$ monohaloalkyl and $C_1-C_4$ polyhaloalkyl.

5. The photochromic article of claim 4 wherein the transparent host material is selected from the group consisting of polymers of polyol(allyl carbonate), copolymers of polyol(allyl carbonate) and vinyl acetate, polyacrylates, poly(alkylacrylates), cellulose acetate, cellulose triacetate, cellulose acetate propionate, cellulose acetate butyrate, poly(vinyl acetate), poly(vinyl alcohol), polycarbonate, polystyrene, poly(styrene-methylmethacrylate)copolymers, poly(styrene-acrylonitrile)copolymers, and polyvinyl butyral.

6. The photochromic article of claim 5 wherein the transparent host material is selected from poly[diethylene glycol bis(allyl carbonate)] and its copolymers with vinyl acetate.

7. The photochromic article of claim 5 wherein the photochromic compound is represented by the graphic formula:

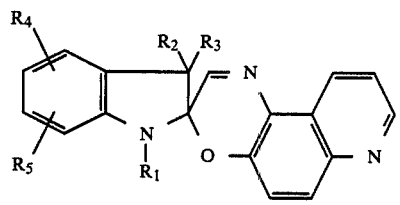

wherein:
(a) $R_1$ is selected from the group consisting of $C_1-C_4$ alkyl, phenyl and benzyl,
(b) $R_2$ and $R_3$ are each selected from $C_1-C_5$ alkyl,
(c) $R_4$ is selected from the group consisting of hydrogen, $C_1-C_2$ alkyl, chlorine, fluorine $C_1-C_5$ alkoxy and $C_1-C_4$ trihaloalkyl, and
(d) $R_5$ is trihaloalkyl.

8. A photochromic article comprising a solid transparent polymerized organic host material selected from the group consisting of polycarbonate, polymers of polyol (allyl carbonate), copolymers of polyol(allyl carbonate) and vinyl acetate, polymethylmethacrylate, cellulose acetate, cellulose propionate, cellulose butyrate, cellulose acetate butyrate, polystyrene, poly(styrene-methylmethacrylate)copolymer, and poly(styrene-acrylonitrile)copolymer, containing a photochromic amount of a photochromic compound represented by the graphic formula:

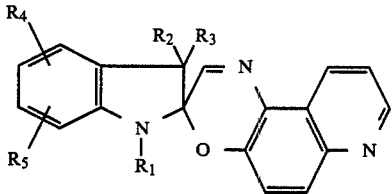

wherein:
(a) $R_1$ is selected from the group consisting of $C_1-C_4$ alkyl, phenyl and benzyl,
(b) $R_2$ and $R_3$ are each selected from $C_1-C_5$ alkyl,
(c) $R_4$ is selected from the group consisting of hydrogen, $C_1-C_2$ alkyl, chlorine, fluorine $C_1-C_5$ alkoxy and $C_1-C_4$ trihaloalkyl.
(d) $R_5$ is selected from the group consisting of $C_1-C_4$ trihaloalkyl.

9. The photochromic article of claim 8 wherein $R_1$ is $C_1-C_4$ alkyl, $R_2$ and $R_3$ are each methyl or ethyl, $R_4$ is trifluoromethyl, fluorine, chlorine hydrogen, methyl, ethyl or methoxy and $R_5$ is trifluoromethyl.

10. The photochromic article of claim 8 wherein the photochromic compound is present in amounts of from 0.05 to 10 weight percent.

11. The photochromic article of claim 10 wherein the host material is selected from poly[diethylene glycol bis(allyl carbonate)] and its copolymers with vinyl acetate.

12. The photochromic article of claim 11 wherein the copolymer is from 80–90 percent diethylene glycol bis(allyl carbonate) and 10–20 percent vinyl acetate.

* * * * *